(12) United States Patent
Fung et al.

(10) Patent No.: US 7,529,338 B2
(45) Date of Patent: May 5, 2009

(54) METHOD AND APPARATUS FOR INSPECTING CIRCUIT BOARDS

(75) Inventors: Leon Fung, San Diego, CA (US); Glenn Olaes, San Diego, CA (US); Frank Silva, Carlsbad, CA (US); Fred Schlieper, Poway, CA (US)

(73) Assignee: FocalSpot, Inc., San Diego, CA (US)

( * ) Notice: Subject to any disclaimer, the term of this patent is extended or adjusted under 35 U.S.C. 154(b) by 54 days.

(21) Appl. No.: 11/677,520

(22) Filed: Feb. 21, 2007

(65) Prior Publication Data

US 2007/0195927 A1  Aug. 23, 2007

Related U.S. Application Data

(60) Provisional application No. 60/775,916, filed on Feb. 22, 2006.

(51) Int. Cl.
*G01N 23/083* (2006.01)
*G01N 23/18* (2006.01)

(52) U.S. Cl. .............................. 378/55; 378/58; 378/208

(58) Field of Classification Search .................. 378/20, 378/51, 53–55, 57, 58, 195, 208
See application file for complete search history.

(56) References Cited

U.S. PATENT DOCUMENTS

| | | | | |
|---|---|---|---|---|
| 3,488,495 A | * | 1/1970 | Schneeman | 250/515.1 |
| 4,809,308 A | * | 2/1989 | Adams et al. | 378/98.2 |
| 4,974,249 A | * | 11/1990 | Zweig | 378/190 |
| 5,463,667 A | | 10/1995 | Ichinose et al. | |
| 5,493,594 A | * | 2/1996 | Hamada et al. | 378/34 |
| 5,541,856 A | * | 7/1996 | Hammermeister | 378/196 |
| RE35,423 E | | 1/1997 | Adams et al. | |
| 6,485,176 B1 | * | 11/2002 | Chen et al. | 378/193 |
| 6,823,040 B1 | | 11/2004 | Teraoka | |

* cited by examiner

*Primary Examiner*—Edward J Glick
*Assistant Examiner*—Thomas R. Artman
(74) *Attorney, Agent, or Firm*—Knobbe Martens Olson & Bear LLP

(57) ABSTRACT

An apparatus and method for inspecting a sample is described. The apparatus can have an X-ray source and detector, a housing, an access aperture in the housing, an access door covering the access aperture, and a stage positionable to extend through the access aperture to a load/unload point outside the housing. The method can include opening the first access door, moving at least a portion of a stage through the first access aperture to a position outside of the housing to receive the sample, moving the stage into the housing, closing the first access door, moving the stage to a position for inspection of the sample, applying X-rays to the sample, receiving X-rays passing through the sample with the X-ray detector, generating one or more signals based on the received X-rays, and displaying an image of the sample for analysis based on the one or more signals.

18 Claims, 13 Drawing Sheets

METHOD AND APPARATUS FOR INSPECTING CIRCUIT BOARDS

PRIORITY APPLICATION

This application claims priority to U.S. Provisional No. 60/775,916, entitled "Method and Apparatus for Inspecting Circuit Boards" filed Feb. 22, 2006, which is incorporated by reference herein in its entirety.

BACKGROUND

1. Field

The field of the invention relates to circuit board inspection systems and methods. More specifically, the invention relates to x-ray systems for inspecting structural aspects of solder connections on circuit boards and inspection techniques.

2. Description of the Related Technology

Improvements in IC packaging technology have facilitated the tremendous increase in the performance of computers, PDAs, cellular phones, audio and video devices, and other equipment that use integrated circuits. The requirements for faster and more powerful chips for such devices necessitates increasing the density of packages for mounting IC chips. With the current trend of high density mounting of electronic parts on a substrate, the pitch of the leads has become smaller and the quantity of solder used for connecting these parts has also decreased. Because of the high density of the parts and their small size, inspecting solder connections has become increasingly difficult. In addition, functionally testing a circuit board to determine if its solder connections are adequate or troubleshooting a faulty board can result in severe damage to components on the board due to faulty solder connections.

As an alternative, X-ray inspection systems and methods can be used to inspect circuit boards to identify faulty solder joints and facilitate circuit board repair. Typically, such X-ray inspection systems include a loading process that requires the sample (e.g., a circuit board) to be attached to a surface or a device which holds the sample in a position for inspection inside a housing of the inspection system. The sample loading and unloading process can be arduous and slow due to the time required to place the sample inside the inspection system, and the need to mount the sample on a surface or in a device for the inspection. Often doors used to access the interior of the inspection system are large and heavy, and the position in which the sample is to be mounted is not easily reachable. Improvements to X-ray systems that address the above-described problems and other problems in the art, and that facilitate more flexible and efficient inspection procedures, are needed.

SUMMARY OF CERTAIN EMBODIMENTS

The systems, methods, and devices of the invention each have several aspects, no single one of which is solely responsible for its desirable attributes. Without limiting the scope of this invention, its more prominent features will now be discussed briefly. After considering this discussion, and particularly after reading the section entitled "Detailed Description of Certain Embodiments" one will understand how the features of this invention provide advantages over other inspection systems. Apparatus and methods for inspecting circuit boards with X-ray inspection systems that provide easier and faster load/unload features would have a wide range of use in many applications, and it would be beneficial in the art to utilize such features to improve current inspection systems and/or exploit the features in new products that have not yet been developed.

In the following description, specific details are given to provide a thorough understanding of the examples. However, it will be understood by one of ordinary skill in the art that the examples may be practiced without these specific details. For example, mechanical and electrical components may be shown in block diagrams in order not to obscure the examples in unnecessary detail. In other instances, components, structures and techniques may be shown in detail to further explain the examples.

In one embodiment, the invention includes an inspection apparatus, including an X-ray source and an X-ray detector, where the X-ray source and X-ray detector are positioned relative to each other such that a sample can be placed between them and such that X-rays emitted from the X-ray source passing through the sample can be detected by the X-ray detector, a positioning table comprising a stage configured to support a sample, the stage being positionable in an xy plane between the X-ray source and the X-ray detector for inspecting the sample, a housing enclosing the X-ray source, the X-ray detector, and the stage when the stage is positioned for inspecting a sample, a first access door connected to the housing, the first access door configured to be movable to an open position for loading and unloading the stage and to a closed position for inspecting the sample and a first access aperture disposed in the housing, where the size of the first access door corresponds to the size of the first access aperture to prevent X-rays from exiting the housing through the first access aperture, and where the stage is further positionable from the interior of the housing so as to extend through the first access aperture to a position exterior to the housing for loading and unloading a sample. In one aspect, the stage includes an attachment means for connecting the sample to the stage. In another aspect, the position exterior to the housing is such that at least a portion of the stage is positioned at least five inches outside of the housing. In another aspect, the position exterior to the housing is such that at least a portion of the stage is positioned at least ten inches outside of the housing. In one aspect, the positioning table can be configured such that the stage can be moved to a position outside of the housing for loading and unloading a sample. The first access aperture can be about at least about three inches wide and at least about twenty-five inches long. The first access aperture can be advantageously disposed between about twenty inches and about forty-five inches above a lowest portion of the housing for ease of loading and unloading the stage.

The housing of the inspection apparatus can include a first portion configured as an operator station for controlling inspection of a sample, the operator station including a stage controller adapted to move the stage for inspecting the sample and to move the stage to a location interior to the housing and adjacent to the first access door in preparation for loading or unloading a sample, and to move the stage from a location interior to the housing and adjacent to the first access door to a position between the X-ray source and the X-ray detector for inspection of the sample. The apparatus can also include one or more interlocks adapted to prevent the stage controller from moving the stage when the first access door is placed in the open position. In another aspect, the positioning table is configured to be controlled by the stage controller to move the stage in an xy plane when the first access door is in the closed position, and the positioning table is further configured to be controlled manually to move the stage when the first access door is in the open position. In another aspect, the apparatus includes a second access door connected to the housing, and a second access aperture disposed in the housing such that the stage is accessible for loading samples through the second access aperture, where the second access aperture is greater in length than the first access aperture to accommodate loading and unloading of a sample too large to fit through the first access door. In another aspect the apparatus can include a window disposed in the housing for visually sighting a sample while it is being inspected. The apparatus can further include a computer configured with inspection software, the computer being further configured to receive signals generated by the X-ray detector, wherein the inspection software is configured to generate images of the sample based on the signals received from the X-ray detectors, and a display connected to the housing, the display in communication with the computer for displaying the images of the sample during inspection.

In another aspect, the apparatus can include a sample manipulator connected to the stage, the sample manipulator configured to hold a sample at an angle relative to the xy plane of the stage movement, and further being configured to rotate the sample to one or more angles relative to the xy plane. In another aspect, the apparatus can include a source translation table connected to the X-ray source and configured to move the X-ray source along an imaging axis between the X-ray source and the X-ray detector to change the distance between the stage and the X-ray source, a detector translation table connected to the X-ray detector and configured to move the X-ray detector along the imaging axis to change the distance between the stage and the X-ray detector, and a tilt plate connected to the source translation table and the detector translation table, the tilt plate configured to hold the X-ray source and the X-ray detector at a fixed position relative to each other along the imaging axis, and a tilt assembly comprising a gear box, the tilt assembly configured to rotate the X-ray source and the X-ray detector about the stage in a plane perpendicular to the xy plane so as to irradiate a sample on the stage at an oblique angle. In another aspect, the X-ray detector includes a focusing element and a zoom element.

Another embodiment includes a method of inspecting a sample with an X-ray inspection system having an X-ray source and an X-ray detector positioned relative to each other so that a sample can be placed there between and so that X-rays emitted from the X-ray source passing through the sample can be detected by the X-ray detector, the inspection system further having a housing, a first access aperture in the housing, and a first access door covering the first access aperture, the method including opening the first access door, moving at least a portion of a stage through the first access aperture to a position outside of the housing to receive a sample placed thereon, moving the stage into the housing, closing the first access door, moving the stage to a position for inspection of the sample, applying X-rays to the sample, receiving X-rays passing through the sample with the X-ray detector, generating one or more signals based on the received X-rays, and displaying an image of the sample for analysis based on the one or more signals. In one aspect, the method includes moving the stage through the first access aperture by mechanically driving the stage to a first position interior of the housing and adjacent to the first access aperture, and then manually (e.g., for example, by hand) moving the stage from the first position to a second position, the second position being exterior to the housing. The method can also include rotating the sample with a sample manipulator such that x-rays are applied to the sample at varying angles.

In another embodiment, an inspection system for analyzing a sample with X-rays, includes means for moving a portion of a stage through a first access aperture to a position outside of a housing of the inspection system to receive a sample, means for retracting the stage into the housing, means for moving the stage to a position for inspecting the sample, where the first access aperture is disposed in a surface of the housing, means for applying X-rays to the sample, means for receiving X-rays passing through the sample, means for generating one or more signals based on the received X-rays, and means for displaying an image of the sample for analysis based on the one or more signals. In another aspect, the apparatus can include means for rotating the sample before applying X-rays to the sample.

In one embodiment, an X-ray system for inspecting printed circuit board assemblies includes a housing and a positioning table having a stage, the stage being positionable to a load/unload position outside of the housing such that at least a portion of the stage is outside of the housing at the load/unload position. In one aspect of this embodiment, the load/unload position is located such that at least a portion of the stage extends at least five inches outside of the housing when the stage is positioned at the load/unload position.

BRIEF DESCRIPTION OF THE DRAWINGS

FIG. 6 is a left perspective view of a positioning table.

DETAILED DESCRIPTION OF CERTAIN EMBODIMENTS

Figure 1:
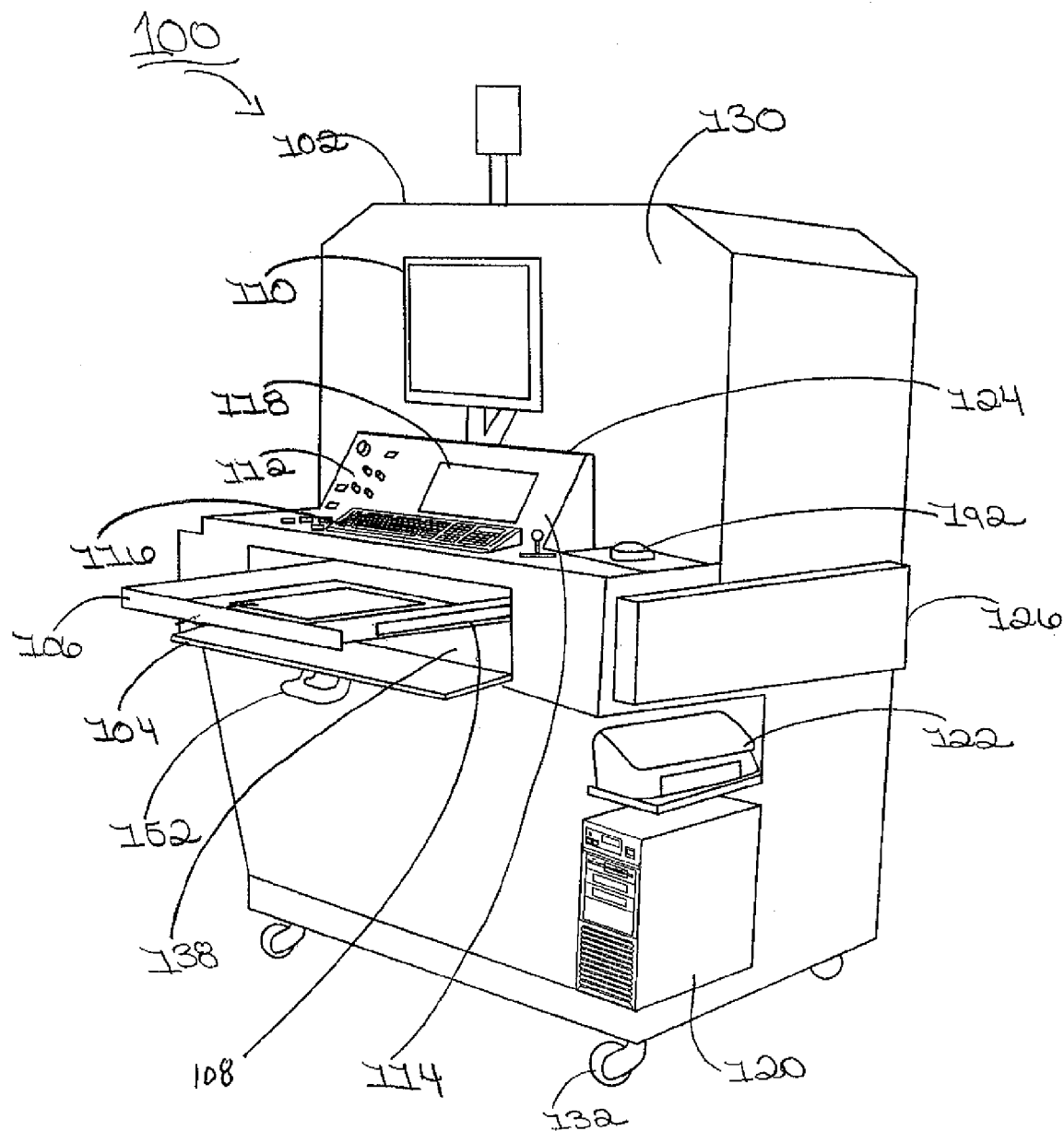
FIG. 1 is a perspective view of an X-ray inspection system.

The following detailed description is directed to certain specific embodiments of the invention that offer improvements to X-ray inspection systems and X-ray processes. However, the invention can be embodied in a multitude of different ways. In this description, reference is made to the drawings wherein like parts are designated with like numerals throughout. For clarity of illustration, the drawing may not illustrate every component in an X-ray inspection system. Rather, the drawings illustrate certain details that may be necessary for one skilled in the art to practice aspects of the invention described herein.

Figure 2:
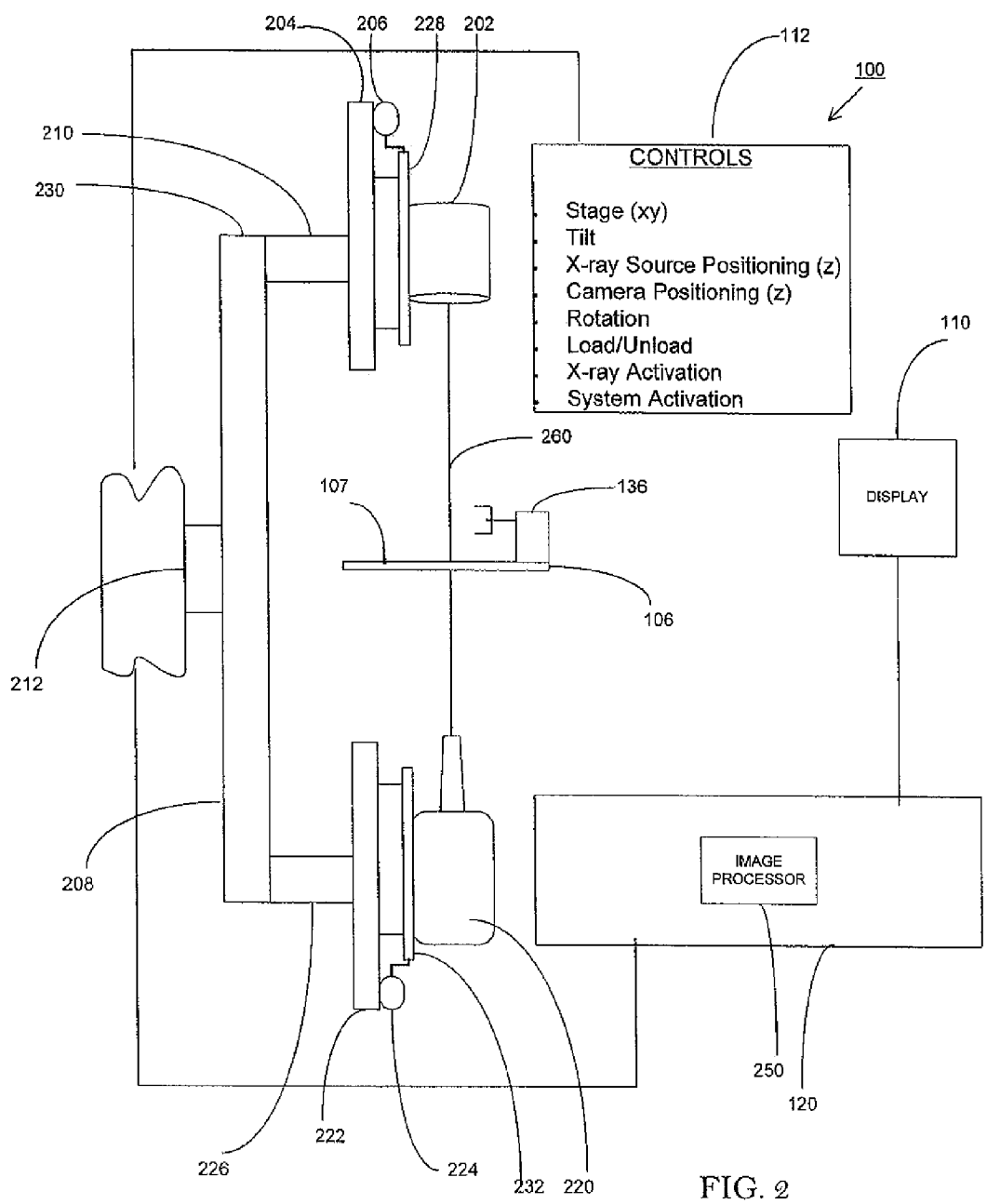
FIG. 2 is a schematic diagram illustrating components of an X-ray system in the inspection system illustrated in FIG. 1.

FIGS. 1 and 2 illustrate features of an X-ray inspection system 100, according to one embodiment of the invention. FIG. 1 is a front perspective view of the x-ray inspection system 100. FIG. 2 is a schematic diagram illustrating some of the components of the inspection system 100. Although described herein in reference to an X-ray inspection system, the features described can also be used for other inspection systems that use a different imaging source, for example, ultraviolet light, infra-red radiation, or the like.

Referring to FIGS. 1 and 2, inspection system 100 includes a housing 102 which encloses and/or holds components of the inspection system 100. In one embodiment, the housing 102 is fabricated from sheet metal and lined with lead to prevent the escape of X-rays through the housing 102. A front portion 130 of the housing 102 is configured as an operator station 124 and includes features that allow a user to operate the inspection system 100 to, for example, inspect solder joints of printed circuit board assemblies ("PCBAs"). The configuration of the operator station 124 allows an operator to quickly and efficiently load and unload a PCBA on a stage 106, position the PCBA in the desired location relative to an X-ray source 202 for inspection, position, adjust and activate an X-ray source 220 and an X-ray detector 202, and view the resulting image of the PCBA while it is being inspected.

The operator station 124 includes controls 112, a window 118 disposed in the housing 102, a display screen 110 attached to the housing 102, a keyboard 116, a mouse 192, a stage positioning joystick (sometimes referred to herein as a "stage controller") 114, and a first access door 104. The position of the features of the operator station 124 are illustrated in one possible configuration for ease of use by an operator, however, in some embodiments these features can be disposed in other positions on or attached to the housing 102. The controls 112 allow an operator to operate a variety of system functions, including the activation and deactivation of the X-ray source 220, and the tilt of an X-ray source 220 and an X-ray detector 202 relative to the position of a sample placed on the stage 106 during inspection of the sample. The controls 112 also control the positioning of the X-ray source 220 and the X-ray detector 202 along an imaging axis 260, discussed further below, and the rotation of the sample by a sample manipulator 136 attached to the stage 106. The X-ray components, including the X-ray source, the detector (e.g., a camera and a zoom lens) can be selected from one of several manufacturers who make such products and that are suitable for the particular inspection application. For example, for inspecting solder joints of PCBAs, the radiation source can be a 80 kV, 90 kV, or 130 kV X-ray source.

The window 118 is disposed at a position in the housing 130 such that an operator working at the operator station 124 can visually view a sample while it is being inspected. The window 118 is manufactured with a material that prevents transmission of X-rays through the window 118. The display screen 110 can be attached to the housing 130 in a location vertically above window 118 to allow an operator to easily view the sample through the window 118 and on the display screen 110. In other embodiments, the display screen 110 can be positioned beside the window 118, or in another convenient location for viewing by an operator. The display screen 110 is connected to a computer 120 and displays information relating to the inspection being performed. For example, the display 110 can show one or more images of the sample as generated by a computer 120 based on the X-rays received by the X-ray detector 202. In the illustrated embodiments, the computer 120 is disposed on the right side of the housing 102 in a computer nook.

The joystick 114 is configured to allow the operator to move the stage 106 in an xy-plane to position the desired portion of a sample between the X-ray source 220 and X-ray detector 202 for inspection. The joystick 114 also allows the operator to move the stage 106 to a position interior to the housing 102 and adjacent to the first access door 104 in preparation for loading or unloading a sample on the stage 106. The first access door 104 is attached to the housing 102 and corresponds to a first access aperture 138 such that when the first access door 104 is placed in a closed position it can block X-rays from escaping through the first access aperture 138. The first access door 104 can be attached to the housing using one or more attachment devices (not shown in FIG. 1 or 2) that allow the first access door 104 to be placed in an open position for loading or unloading a sample, or a closed position for inspection. The attachment devices can include, for example, hinges or another mechanical pivoting device, or rails that slide the first access door 104 to one side of the first access aperture 138. In another embodiment, the first access door 104 is configured to be partially or completely removable from the housing 102 for access to the first access aperture 138.

While inspecting a sample, the first access door 104 is placed in closed position over the first access aperture 138. The first access door 104 is lead-lined to prevent X-rays from escaping through the first access aperture 138. To gain access to the stage 106, the joy stock 114 is used to move the stage 106 to a position adjacent to the first access door 104 and interior to the housing 102. The first access door 104 can be placed in an open position exposing the stage 106 through the first access aperture 138 and allowing access to a handle 152 connected to the stage 106. The handle 152 can be used to manually move a portion of the stage 106, or all of the stage 106, through the first access aperture 138 to a position exterior to the housing 102. Various embodiments of the inspection system may allow the stage 106 to be moved to different positions outside of the housing 102, for example, so that the stage 106 is positioned partially or fully outside of the housing 102 in the load/unload position. In one embodiment, the stage 106 includes a clampless sample support 107 such that a sample placed on the stage 106 is supported but not mounted onto or attached to the stage 106, allowing the sample to be quickly loaded or unloaded. The clampless sample support 107 can be rectangular planar surface with a smooth or textured finish manufactured of a material that will have minimal interference with X-rays. In some embodiments, the stage 106 includes means for attaching a sample to the stage 106, for example, using one or more clips, clamps, a sample manipulator, or the like.

As illustrated in FIG. 1, a portion of the stage 106 may be positioned at a location exterior to the housing 102 in a position allowing an operator to access the stage 106 to load or unload samples. In some embodiments, at least a portion of the stage 106 can be moved to a position at least about five inches exterior to the housing 102 to allow the stage 106 to be accessible for loading and/or unloading samples. In some embodiments, at least a portion of the stage 106 can be moved to a position about at least ten inches exterior to the housing 102, or to a position of about at least fifteen inches exterior to the housing 102. An xy positioning table 108 moves the stage 106 in a substantially horizontal xy plane during the inspection and also moves the stage 106 into position for loading and unloading a sample. The sample manipulator 136 can be optionally connected to the stage 106 and is used to hold a sample at a desired angle relative to the xy plane in which the stage 106 can be positioned while the sample is being inspected. The sample manipulator 136 is also controllable by controls 112 and can rotate the held sample about an axis passing through the sample manipulator 136 to a desired position for inspecting the sample.

The inspection system 100 also includes wheels 132 attached to the bottom of the housing 102 which allows the inspection system 100 to be easily moved within an inspection facility despite its weight. The inspection system 100 further includes a printer 122 connected to the computer 120. The printer 122 is used to print reports, images, results and other information related to inspection of a sample.

A second access door 126 covering a second access aperture (not shown) is disposed on the right side of the housing 102. In another embodiment, the second access door 126 can be disposed on the left side of the housing 102. The second access door 126 allows access to the interior of the inspection system 100, and in particular, access to the stage 106 when it is positioned inside the housing 102. The second access aperture is typically configured to be larger than the first access aperture 138, for example longer and/or wider than the first access aperture 138, so that samples which will not fit through the first access aperture 138 can be placed into the housing 102 through the second access aperture and positioned between the X-ray source 220 and the X-ray detector 202 for inspection. Both the first access door 104 and the second access door 126 can be configured with at least one interlock device that disables the operation of the x-ray source 220 and the xy positioning table 108 when either door is opened.

FIG. 2 illustrates that the X-ray source 220 and the x-ray detector 202 are aligned along an imaging axis 260 such that x-rays emitted from the x-ray source 220 and through a sample held by the stage 106 are detected by the x-ray detector 202. A tilt assembly 230 includes a tilt plate 208 which is configured to tilt X-ray source 220 and X-ray detector 202 to the left and right about the stage 106 in a plane perpendicular to the stage 106. The tilt assembly 230 also includes a tilt mechanism 212 connected to the tilt plate 208 and allows movement of the tilt plate 208 so that the X-ray source 220 and X-ray detector 202 can be tilted in a plane perpendicular to the xy plane of the stage 106 movement to produce an image of the sample at one or more oblique angles. The tilt mechanism 212, further described in reference to FIGS. 11-13, includes a gearbox that drives the movement of the tilt plate 208 and prevents undesirable movement of the tilt assembly 230 while it is in motion. The movement of the tilt assembly 230 is controlled by controls 112.

The x-ray source 220 and x-ray detector 202 are held in an aligned position along the imaging axis. The tilt plate 208 supports the x-ray detector 202 and the x-ray source 220. The x-ray detector 202 is connected to the tilt plate 208 by a detector support 210 and detector translation table 204. The x-ray detector 202 can be moved along the imaging axis to a position either closer to or further from the stage 106 by a detector translation table 204. Driver 206 is attached to the detector translation table 204 and provides the driving means to move the detector translation table 204 and position the x-ray detector 202 at a desired location along the imaging axis 260, e.g., either closer to or further away from the sage 106. The X-ray source 220 is connected to the tilt plate 208 by a source support 226 and a source translation table 222. A driver 224 moves the source translation table 222 to position the X-ray source 220 along the imaging axis 260 to a desirable position, e.g., either closer or further from the stage 106. The source translation table 222 and the detector translation table 204 are controlled by the controls 112.

FIG. 2 also shows the computer 120 connected so as to receive signals from the X-ray detector 202. In this embodiment, the X-ray source 220 is positioned below the stage 106 and the X-ray detector 202 is positioned above the stage. In some embodiments, the positions are reversed so that an X-ray source is positioned above the stage and the detector is positioned below the stage. The computer 120 is configured with hardware and software to receive the signals from the X-ray detector 202, capture frames depicting the sample being inspected, analyze and/or adjust the captured frames and generate images, and provide the images to the display screen 110 for viewing by an operator in near real-time. The computer 120 can be any suitable configured computer, for example an IBM-PC compatible computer, an Apple computer, or the like. In one embodiment, the computer 120 is an IBM-PC compatible mini tower computer configured with a compact disc writer, Ethernet 10/100 base-T capability for network connectivity, and running a Windows™ XP operating system. The computer 120 can be configured with any available image processing software for receiving signals from the detector, and generating images based on the received signals. The image processing software can provide analysis tools to help an operator determine information from the generated images, for example, information that can help an operator identify faulty solder joints.

The functionality of the x-ray system is controlled by controls 112, which are configured on a control panel in the operator station as illustrated in FIG. 1. The controls 112 allow an operator of the x-ray system to inspect a sample, including controlling the activation of the X-ray source 220, and the tilt of the x-ray source 220 and x-ray detector 202 relative to the stage 106, which is further described in reference to FIG. 3. The controls 112 control tube variable positioning of the X-ray detector 202, for example, allowing an operator to move the x-ray detector 202 along the imaging axis 260 (e.g., in a direction referred to as "Z1") by activating driver 206 and moving the detector translation table 204 to position the x-ray detector 202 in a desired position for inspection. The controls 112 further control tube variable positioning of the X-ray source 222, for example, allowing an operator to move the x-ray source 220 along the imaging axis 260 (in a direction referred to as "Z2)" by activating driver 224 and moving the source translation table 222 to a desired position. Additionally, the controls 112 also control zoom and focusing functions of the X-ray detector 202.

Figure 3:
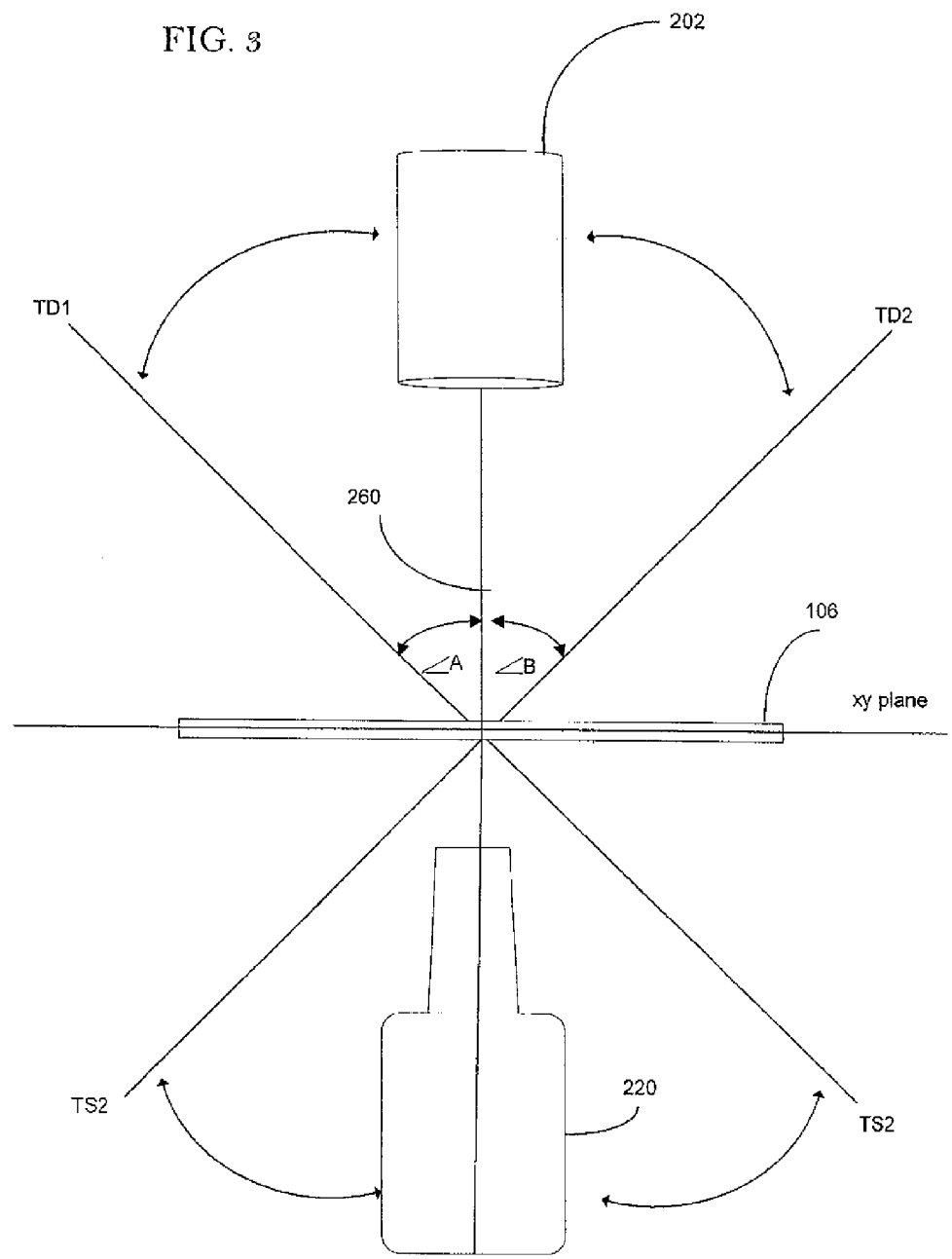
FIG. 3 is a schematic diagram illustrating a range of tilt angles at which an X-ray source and an X-ray detector can be positioned.

FIG. 3 is a schematic diagram illustrating a range of tilt angles in which the X-ray source 220 and the X-ray detector 202 can be positioned about the stage 106 to inspect a sample. The X-ray source 220 and the X-ray detector 202 are configured to tilt off-axis in relation to the sample position providing oblique object viewing. As described above, X-ray source 220 and X-ray detector 202 can be positioned at various locations along the imaging axis 220 and are aligned relative to each other along the imaging axis 260. An image formed by the inspection system for analysis depicts the sample in an imaging plane that is perpendicular to the imaging axis 260. FIG. 3 illustrates the X-ray source 220 and an X-ray detector 202 in a first position (centered) about the stage 106 such that the imaging axis 260 is perpendicular to an xy plane in which the stage 106 can be positioned. In this position, angles A and B are both about 90°, and this can be referred to as a 90° inspection angle. X-rays emitted from the X-ray source 220 and passing through a sample on the stage 106 are detected by the detector 202 and used to form an image of the sample in an imaging plane that is perpendicular to the imaging axis 260, and in this case the imaging plane is parallel to the xy plane.

For some inspections, it is desirable to change the inspection angle to analyze an image of the sample where the imaging plane is not parallel to the xy plane. To change the inspection angle, the X-ray source 220 and X-ray detector 202 can be rotated about the stage 106 so that the imaging axis 106 is tilted at an oblique angle relative to the stage 106 and the xy plane. For example, the X-ray source 220 can be positioned at tilt position TS1 and the X-ray detector 202 positioned at corresponding tilt position TD1 to inspect a sample at an oblique inspection angle A. The X-ray source 220 can also be positioned at tilt position TS2 and the X-ray detector 202 positioned at corresponding tilt position TD2 to inspect a sample at an oblique inspection angle B. In various embodiments, the inspection angle can be about zero to ninety degrees, and is only limited by the particular configuration of the inspection system, for example, the mechanical connection of the tilt plate 208 to a tilt mechanism 212 (FIG. 2), the size of the housing 102, or the position of other equipment in the housing 102. In this embodiment, the inspection system is configured to use inspection angles of between about 40° and about 90°, which is generally sufficient for inspecting most samples, including most samples of solder joints on PCBAs.

Figure 4:
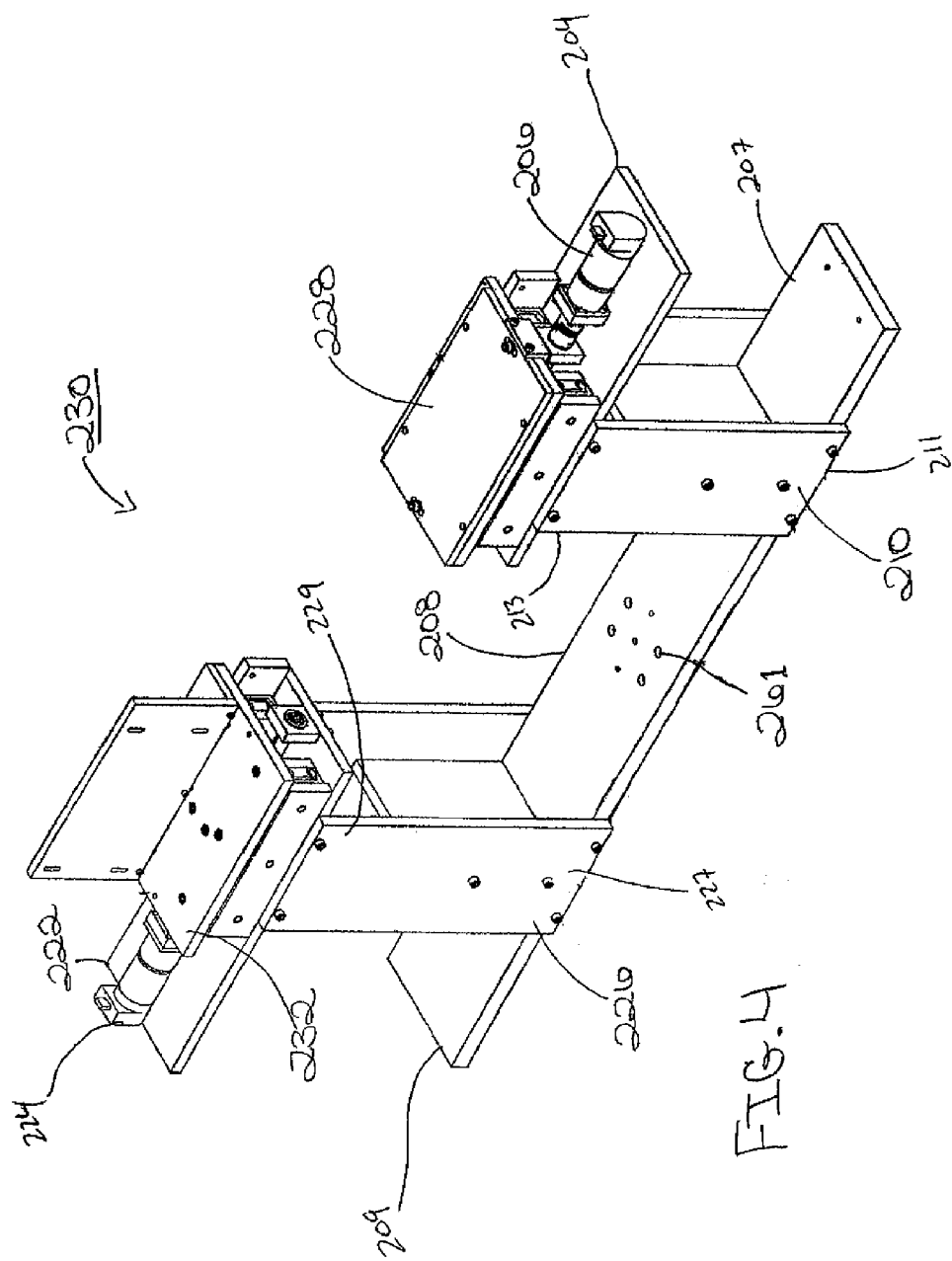
FIG. 4 is a perspective view of a tilt assembly that can be used in the inspection system illustrated in FIG. 1.

FIG. 4 is a perspective view of one embodiment of the tilt assembly 230 without an x-ray source or an x-ray detector attached to it. The tilt assembly 230 includes a generally rectangular rigid tilt plate 208 having attachment holes 261 for attaching to a rotational or tilt mechanism 212 (FIG. 2). A first end 211 of the detector support 210 is rigidly connected near a first end 207 of the tilt plate 208 such that it extends perpendicular to the tilt plate 208, the first end 207 of the tilt plate 208 being located above the stage 106 when the tilt assembly 230 is positioned in the housing 102. A first end 227 of the source support 226 is connected near a second end 209 of tilt plate 208 such that it extends perpendicular to the tilt plate 208, on the same side of the tilt plate 208 as detector support 210, and parallel to the detector support, the second end 209 of the tilt plate 208 being located below the stage 106 when the tilt assembly 230 is positioned in the housing 102. The detector translation table 204 is connected to a second end 213 of the detector support 210, The position of the detector translation table 204 on the detector support 210 is such that the detector translation table 204 moves an attached detector in a direction substantially parallel to a longitudinal axis of the tilt plate 208 which is also parallel to the imaging axis 260. The source translation table 222 is connected to a second end 229 of the source support 226. The position of the source translation table 222 on the detector support 210 is such that the source translation table 204 moves an attached X-ray source in a substantially parallel direction to a longitudinal axis of the tilt plate 208. The supports 226, 210 and the translation tables 222, 204 are sized such that the X-ray source 220 and the X-ray detector 202 are aligned along the imaging axis 260 (e.g., FIG. 2) when attached to their respective translation tables 222, 204.

The detector translation table 204 includes detector plate 228 which is configured to be movable along an axis parallel to the longitudinal axis of the tilt plate 208 by driver 206, such that an X-ray detector can be connected to the detector plate 228 and moved to a position closer or further from a sample placed on the stage 106 using the detector translation table 204. Similarly, source translation table 222 includes source plate 232 which is configured to be movable along an axis parallel to the longitudinal axis of the tilt plate 208 by driver 224, such that an X-ray source can be connected to the source plate 232 and moved to a position closer or further from a sample placed on the stage 106 using the source translation table 222. As one of skill in the art will appreciate, changing the position of an X-ray source and/or an X-ray detector relative to a sample being inspected can change imaging characteristics, for example, source spot size. Positioning of an X-ray source and an X-ray detector using the translation tables 222, 204 can be controlled by the controls 112 (FIG. 1).

Figure 5:
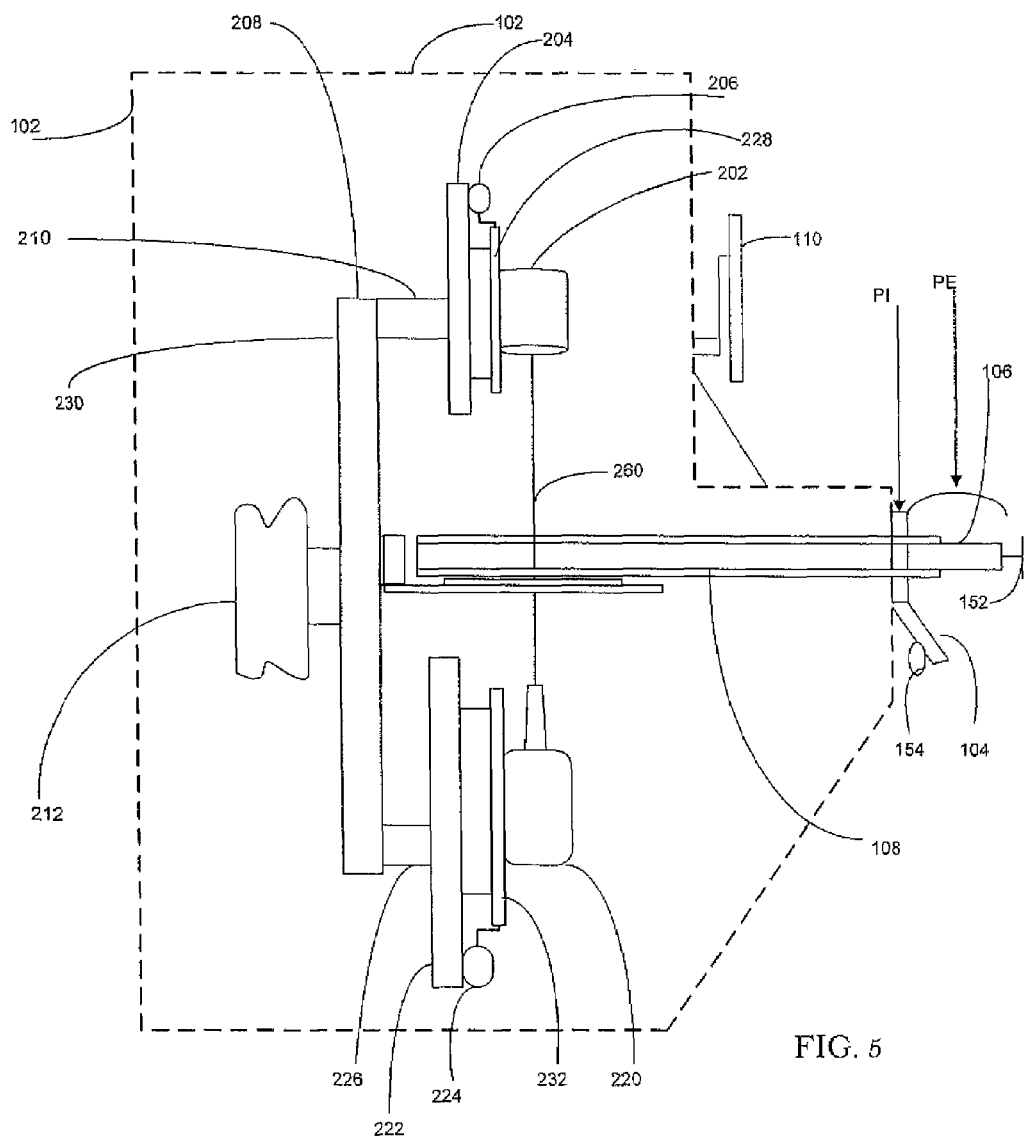
FIG. 5 is schematic diagram illustrating an inspection system showing a stage in a load/unload position exterior to the housing.

FIG. 5 is schematic diagram illustrating a left elevation view of a portion of the inspection system 100. Here, the position of the housing 102 is shown by a dashed line. The first access door 104 is illustrated in an open position allowing at least a portion of the stage 106 to extend through the first access aperture 138 to a position exterior to the housing 102.

A positioning table 108, illustrated in further detail hereinbelow in FIG. 6, is configured to move the stage 106 in a xy plane to a position aligned with the imaging axis 260 to inspect a sample on the stage 106 using the joystick 114 (FIG. 1). Advantageously, the inspection system 100 is configured such that the positioning table 108 can move every portion of the stage 106 in line with the imaging axis 260 so that a sample will not have to be repositioned (e.g., turned 180 degrees) during inspection. However, in cases where a large sample is being inspected, for example, a sample that requires use of the second access door 126 to place the sample interior to the housing 102, inspection of the entire sample may require manually re-positioning the sample, which can be done through the second access door 126.

The positioning table 108 is also configured to move the stage 106 to a position $P_I$ interior to the housing 102 and adjacent to the first access door 104, using the joystick 114. As one of skill in the art will appreciate, the movement of the stage 106 by the positioning table 108 can be accomplished by a variety of automatic or semi-automatic mechanical and/or electrical driving means, including one or more motors (e.g., a step motor configured to provide movement in an x-direction and a step motor configured to provide movement in a y-direction), fluidic systems (e.g., air or fluid), rail systems, belts, pulleys, or movement systems incorporating magnetic devices, air bearings, low friction surfaces, and the like, (generally referred to herein as the "mechanical driving means"). According to one embodiment, the use of such driving means can be controlled by the joystick 114. Some embodiments can use control devices other than a joystick, for example, a ball, toggle switches, a keyboard, a touchpad, a mouse, foot pedals, or another suitable control device.

The positioning table 108 is further configured to allow at least a portion of the stage 106 to be moved to a position $P_E$ exterior to the housing 102. Because the movement of the stage 106 by the positioning table 108 using the joystick 114 and the mechanical driving means can be disabled by an interlock when the first access door 104 is opened, a handle 152 connected to the stage 106 can be used by an operator to manually (e.g., by hand) move the stage 106 from the position $P_I$ through the first access aperture 138 to the position $P_E$ to allow a sample to be placed on the stage or removed from the stage 106. The handle 152 is also used to manually move the stage 106 from the position $P_E$ to the position $P_I$. In some embodiments, the positioning table 108 is not disabled when the access door 104 is opened, and can be used to move the stage 106 to the position $P_E$ outside of the housing 102, and also retract the stage 106 from the position $P_E$ to a position inside the housing 102.

FIG. 6 is a left perspective view of the positioning table 108, according to one embodiment. A rigid back mounting support 169 and a rigid front mounting support 171 are disposed inside the housing 102 such that the surfaces 169, 171 are substantially parallel to each other, and such that a longitudinal axis of the supports 169, 171 extend towards the left and right side of the housing 102 (which in this embodiment can be referred to as the "x-direction"). An x-direction rail 164 is mounted to the back mounting support 169 and a x-direction rail 165 is mounted to the front mounting support 171, the x-direction rails 164, 165 aligned in parallel with each other. The x-direction rails 164, 165 are positioned apart at a distance apart "D" which can be dependent particular embodiment. A carriage 173 includes square-shaped support structure 175 that is movably connected to the x-direction rails 164, 165 and configured to move smoothly in the x-direction along the x-direction rails 164, 165 with a minimal amount of friction and vibration. y-direction rails 162,163 are connected to opposite sides of the support structure 175 and positioned extend towards the front and back of the housing 102 and aligned to be parallel with each other. A stage 106 is movably connected at a right side 179 and a left side 181 to the y-direction rails 162,163 and configured to move smoothly in the y-direction along the y-direction rails 162,163 with a minimal amount of friction and vibration. The positioning table 108 is configured to allow the stage 106 to be positioned towards the front on the housing 102, and through an access aperture 138 in the housing 102 by moving in the y-direction along the y-direction rails 162,163. The clampless support surface 107 is a horizontally oriented surface across the lower portion of the stage 106 on which a sample is placed during inspection, according to one embodiment. In some embodiments, the support surface 107 can be a horizontally oriented surface across another portion of the stage 106, for example, the upper portion of the stage 106. The handle 152 is connected at a front portion of the stage 106 for manually moving the sage 106. The support surface 107 can be configured to be smooth or have a texture, grooves, bumps, dimples, ridges, or other suitable features that can help prevent undesirable movements of a sample that is placed on the sample surface 107 when the stage 106 is positioned for inspection of the sample.

The positioning table 108 can also include an independent driving device for each of the x and y directions. In some embodiments, the positioning table 108 includes a first motor 160 (not shown) and x-screw 161 (not shown) aligned in the x-direction and mounted on the back mounting support 169 and connected to the carriage 173 such that movement of the x-screw 161 by the first motor 160 moves the stage in the x-direction. The positioning table 108 can also include a second motor 185 (not shown) and a y-screw 187 (not shown) positioned, for example, on the interior of the carriage 173, mounted to the carriage 173, aligned in the y-direction and connected to the stage 106 such that movement of the y-screw 187 by the second motor 185 moves the stage in the y-direction. The first and second motors can be controlled by the joystick 114.

Figure 7:
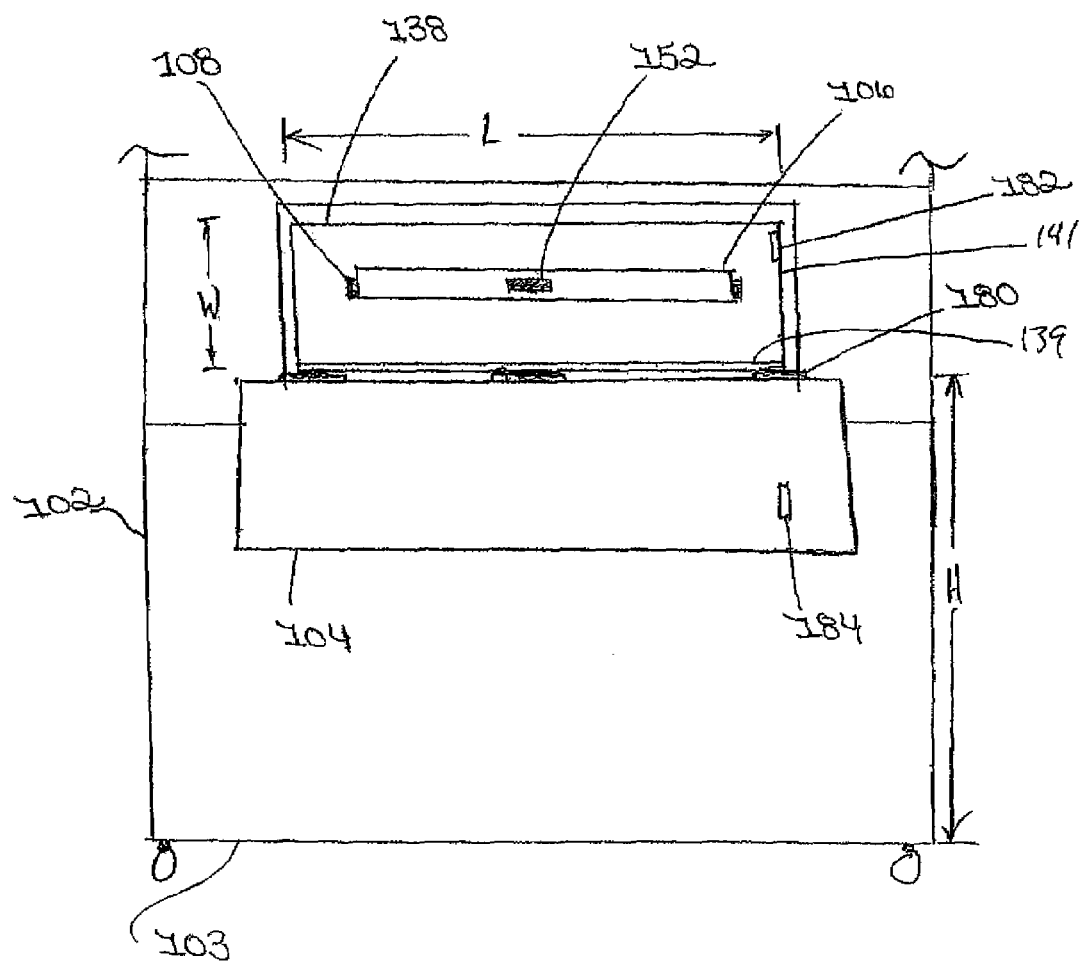
FIG. 7 is a front elevation view of the first access door in an open position.

FIG. 7 is a front elevation view of the first access door 104 in an open position and exposing a front edge of stage 106 through the first access aperture 138. The first access door 104 is attached to the housing 102 by connectors 180 which can be, for example, hinges, such that the first access door 108 swings outward and downward when opened. In some embodiments, the first access door 108 can be configured to swing outward and upward when opened, or to move (e.g., slide or swing) to either the left or right side of the first access aperture 138 when opened. In some embodiments the front access door 104 is removable from the housing 102. Opening the first access door 104 allows access to the interior of the housing 102 through the first access aperture 138, and access to the stage 106. The first access aperture 138 can be configured to be of various sizes, depending on the embodiment. In one embodiment, the first access opening 138 is about 5¾ inches wide (this dimension is depicted by the letter "W" shown in FIG. 7) and about 29½ inches long (this dimension is depicted by the letter "L" shown in FIG. 7) to allow fully populated (e.g., configured on both sides of the board) printed circuit board assemblies of up to about 20 inches by 24 inches to be loaded onto the stage 106 and inspected. However, the dimensions of the first access aperture 138 may be larger or smaller without departing from the scope of the inventive aspects described herein. In some embodiments, the dimensions of the first access aperture 138 can be configured to be between about 1 inch and 10 inches wide, and about 5 inches and 35 inches long, for example, about 3 inches wide by about 25 inches long.

The location of the first access opening 138 relative to the lowest portion of the housing 103 is advantageously at a height that allows an operator to comfortably load and unload samples. According to this embodiment, the first access opening 138 is allocated on the housing 102 at a position where a lower edge 139 of the first access aperture 138 is between about 20 inches and about 45 inches from the lowest portion of the housing 103, and this dimension is depicted by the letter "H" shown in FIG. 7. This is assuming, the lowest portion of the housing 103 is configured relatively close (e.g., about 0 inches to about 5 inches) to a support surface on which the housing 102 sits. In embodiments where the lowest portion of the housing 103 is not close to a support surface on which the housing 102 sits, then the first access opening 138 can be advantageously disposed in the housing 102 at a position where a lower edge of the first access aperture 138 is at a preferred working height, for example of between about 20 inches and about 45 inches.

FIG. 7 also shows an access aperture interlock device 182 disposed on the housing 102 near the first access aperture 138 on the interior edge of wall 114 and a corresponding access door interlock device 184 disposed on the first access door 104 so as to be in contact with device 182 when the door is in the closed configuration. When the inner surface of the first access door 104 is closed, the interlock devices 182, 184 engage to enable the use of one or more functions of the inspection system 100, for example, the joystick 114 to control the movement of the stage 106 and the activation of the X-ray source 220. When the first access door 104 is opened, the interlock devices 182, 184 disengage and disable one or more functions of the inspection system 100, for example, the joystick 114 and the x-ray source 220. Some embodiments can include more than one interlock. The interlock(s) can be configured to affect one or more of the features of the inspection system. In some embodiments, no interlocks are used so that there is no system functionality disabled when the first access door 104 is opened.

Figure 8:
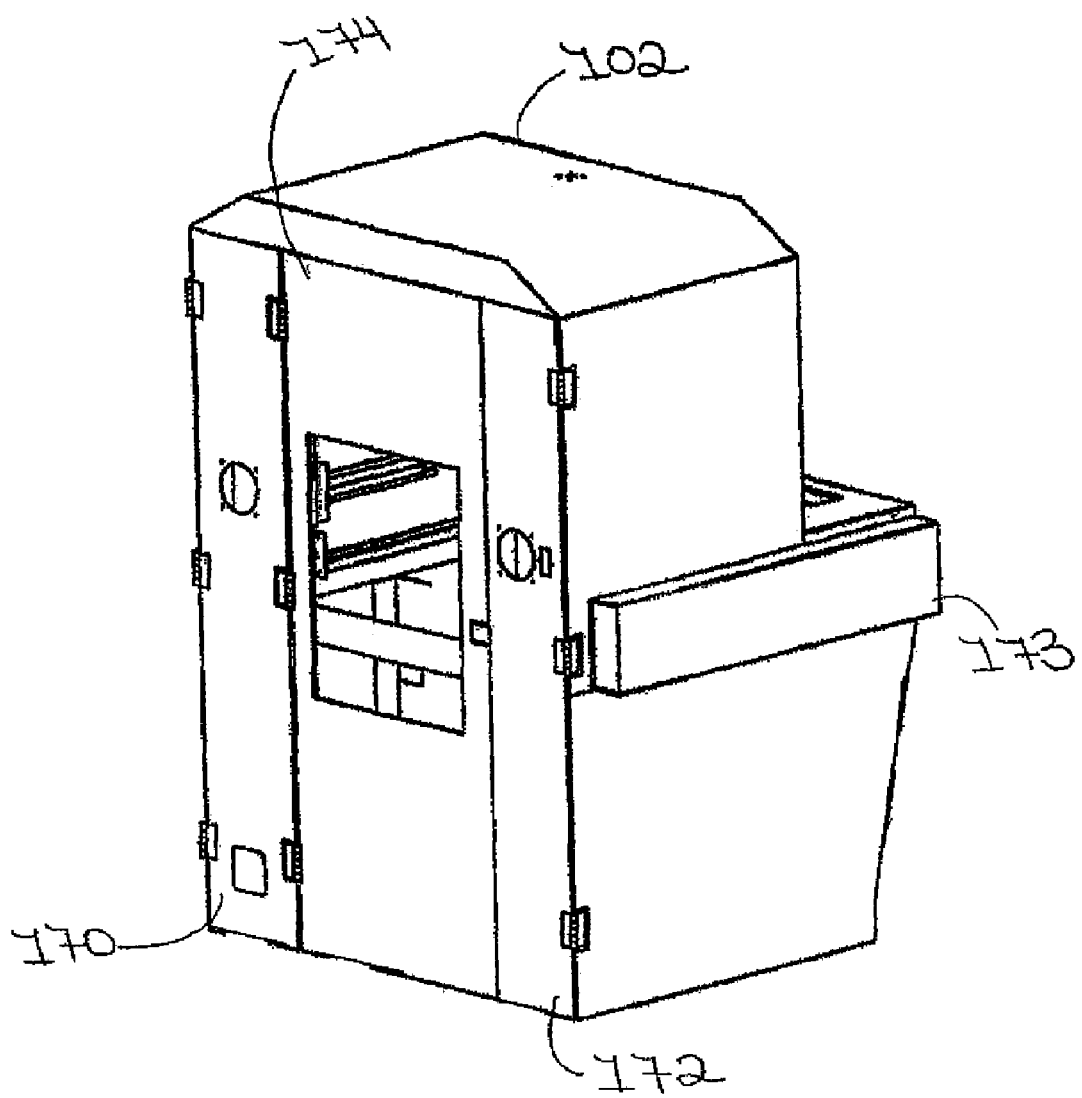
FIG. 8 is a right rear perspective view of a housing of the inspection system of FIG. 1.
Figure 9:
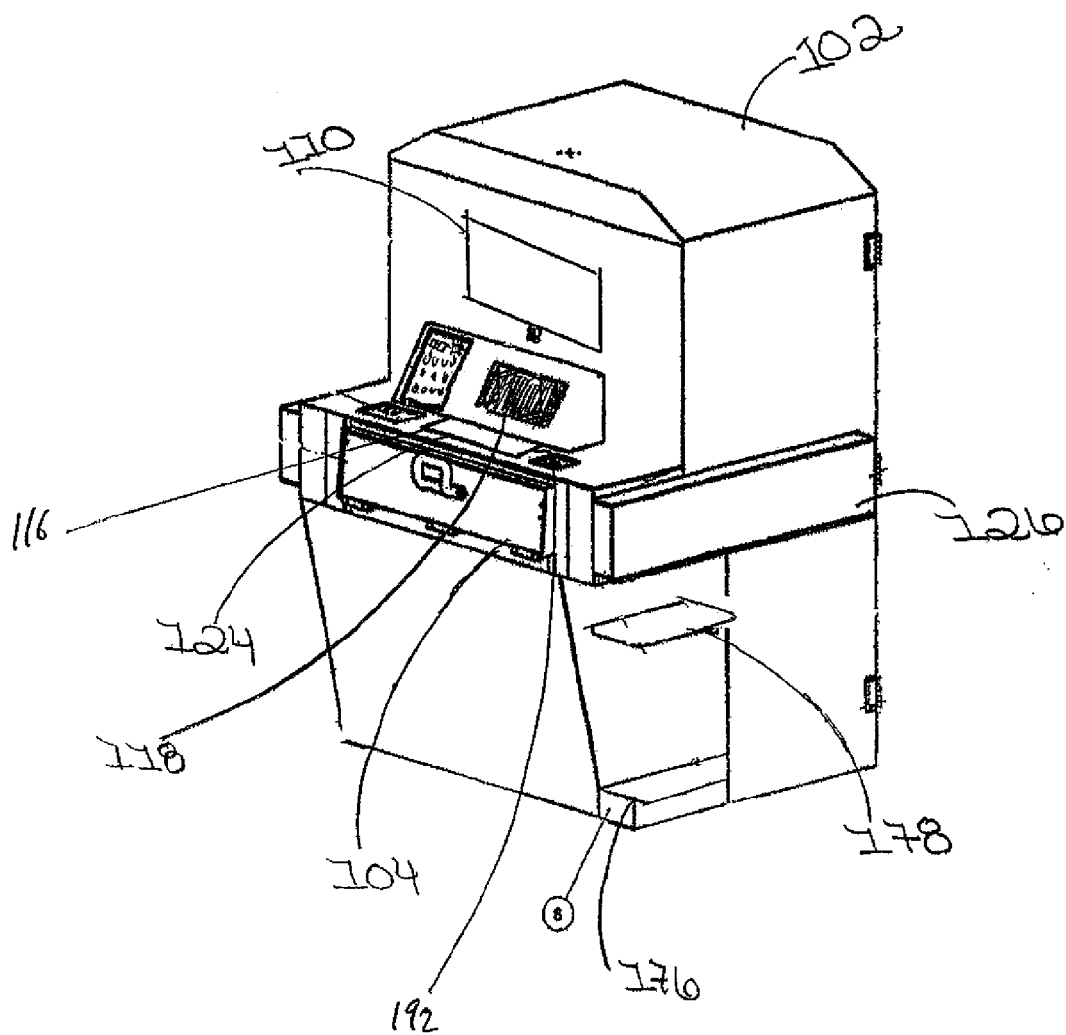

FIG. 8 is a right rear perspective view of the inspection system 100 of FIG. 1. The housing 102 includes a right rear door 172 and a left rear door 170 which can be opened to allow easy access to electrical panels (not shown) disposed inside the housing 102 for maintenance of the inspection system 100. A center rear door 170 is positioned in the center of the rear of the inspection system 100 and allows access to the main enclosure of the housing 102 that contains the positioning table 108, the tilt assembly 230, and the X-ray source 220 and the X-ray detector 202. A third access door 173 is disposed on the left side of the housing 102, and covers a third access opening (not shown) which can be used to access the stage to allow loading of large samples.

Figure 9:
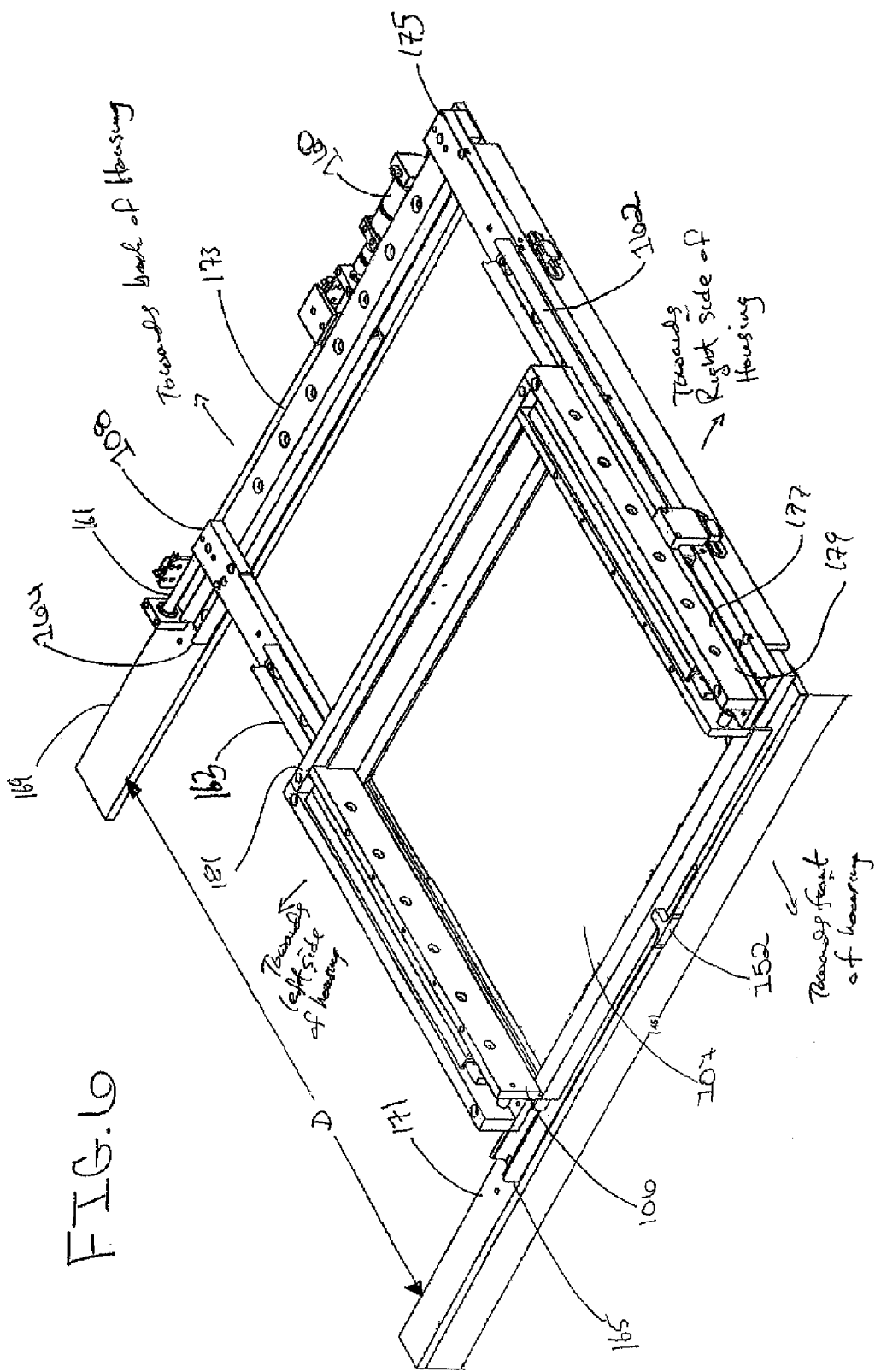
FIG. 9 is a front left perspective view of a housing of the inspection system of FIG. 1.

FIG. 9 is a front left perspective view of the inspection system 100 of FIG. 1. In FIG. 9, the first access door 104 is shown in a closed position. FIG. 9 also shows a computer shelf 176 disposed on a lower right-hand portion of the housing 102 for holding the computer 120 illustrated in FIG. 1. FIG. 9 also illustrates a printer shelf 178 disposed the lower right-hand portion of the housing 102 for holding the printer 122 illustrated in FIG. 1. The configuration as shown allows a printer and a computer to be easily accessed by an operator at the 124. This configuration also allows a computer and a printer to reside within the footprint of the inspection system 100 and allows the inspection system 100 to be moved as a unitary system, rather than as separate components.

Figure 10:
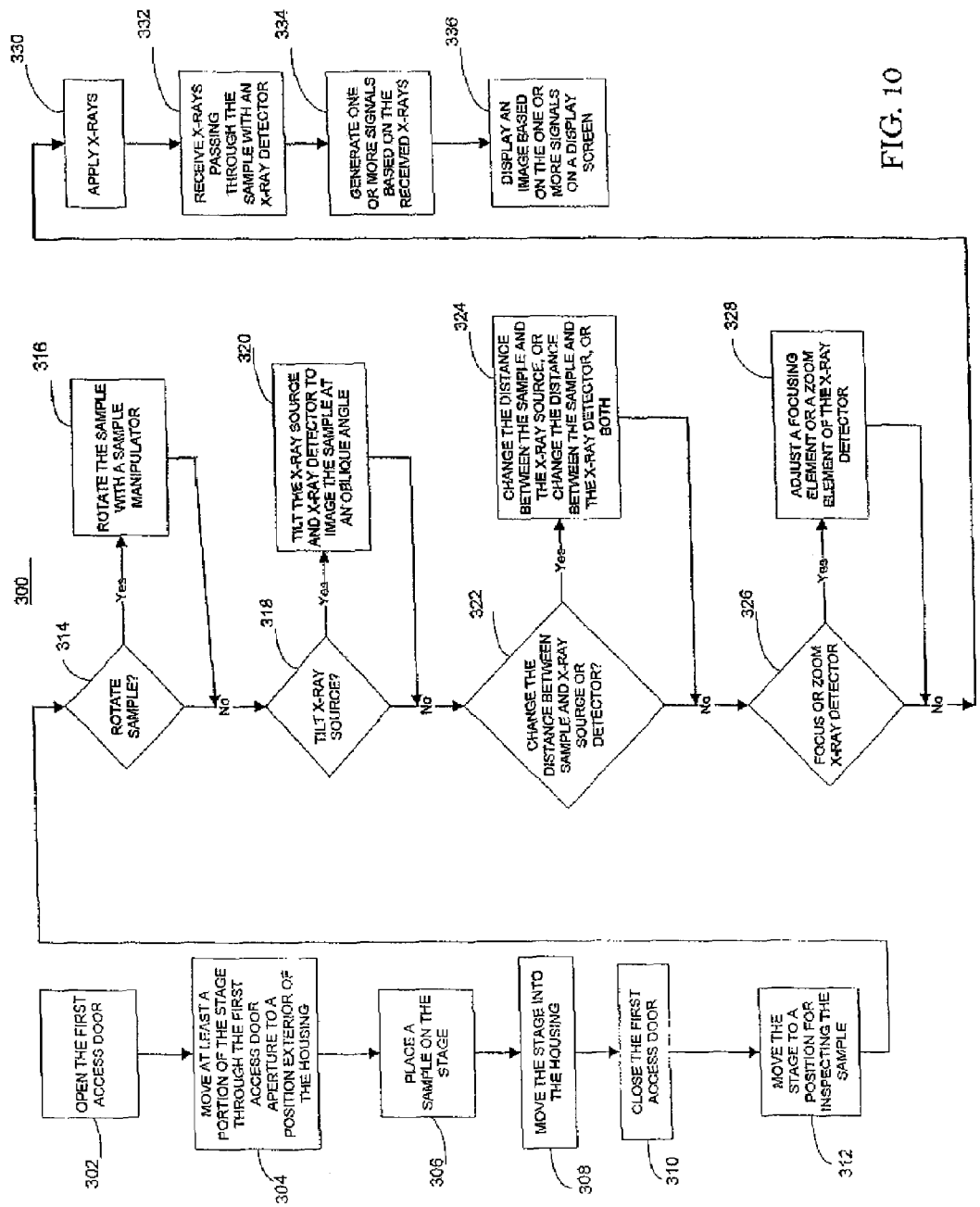
FIG. 10 is a flowchart illustrating a process for inspecting samples.

FIG. 10 is a flowchart illustrating a process 300 for inspecting a sample (for example, a Printed Circuit Board Assembly) with an X-ray inspection system, such as the one described herein and illustrated in the foregoing figures. The inspection system can include an X-ray source 220 and an X-ray detector 202 positioned relative to each other so that a sample can be placed there between and so that X-rays emitted from the X-ray source 220 passing through the sample can be detected by the X-ray detector 202. The inspection system 100 can further include a housing 102, a first access aperture 138 in the housing 102, and a first access door 104 which covers the first access aperture 138 when the door is closed. According to one embodiment, the process 300 can be performed using features described herein relating to the X-ray inspection system 100 and by features and sub-processes that are known to those of skill in the art. The process can be performed by using the features of the operator station 124, including for example, controls 112 for moving, positioning, and adjusting the X-ray source 220 and the X-ray detector, and activating the X-ray source 220, a joystick 114, and a positioning table 108 for moving the stage 106, a sample manipulator 136, a computer 120, a keyboard 116, a mouse 192, and a display screen 110.

At the beginning of the process 300 in state 302, the first access door 104 is opened which uncovers the first access aperture 138. The process 300 then proceeds to state 304, where at least a portion of the stage 106 is moved through the first access aperture 138 to a position exterior to the housing 102 to receive a sample placed thereon. In one embodiment where an interlock disables any type of automated movement of the stage 106 when the first access door 104 is open, the stage 106 is manually moved through the first access aperture 138 by using, for example, a handle attached to the stage. Some embodiments may not use an interlock. In some configurations the stage can be moved through the first access door 104 by mechanical driving means. The process 300 then proceeds to state 306 where a sample is placed on the stage 106. The stage 106 is configured to support a sample without mounting, clamping or attaching the sample to the stage, so that the sample can be quickly placed on and removed from the stage 106. If it is desirable to rotate the sample so that images of the sample can be made at various angles, the sample can be attached to sample manipulator 136 that is attached to the stage 106, according to one embodiment.

In state 308 of process 300, the stage 106 is moved into the housing 102, which can be done manually or with a mechanical driving means. Next, in state 310, the first access door 106 is closed. In state 312 the stage 106 is moved into a position for inspecting the sample on the stage 106. The process 300 then proceeds to state 314 where it determines if the sample manipulator 136 should be used to rotate the sample. If yes, the process 300 proceeds to state 316 where the sample manipulator 136 rotates the sample to a desired angle, and then proceeds to state 318. If no, the process 300 proceeds directly to state 318. In state 318 the process 300 determines whether to tilt the X-ray source 220 to inspect the sample at an oblique angle. If yes, the process 300 proceeds to state 320 where the X-ray source 220 and the X-ray detector 202 are rotated in a plane perpendicular to the xy movement plane of the stage 106 such that they are tilted to image the sample at an oblique angle, and then proceeds to state 322. If no, the process 300 proceeds directly to state 322. In state 322, the process 300 determines if the distance between the X-ray source 220 and the sample should be adjusted, or if the distance between the sample and the X-ray detector 202 should be adjusted. If yes, the process 300 proceeds to state 324 where the X-ray source 220 and/or the X-ray detector 202 are moved. Moving the X-ray source 220 away from the sample increases the spot size, and moving it closer decreases the spot size, and then the process 300 proceeds to state 326. Increasing the distance between the X-ray detector 202 and the sample increases the area of the sample imaged by the X-ray detector 202, decreasing the distance decrease the area of the sample imaged. If no, the process proceeds directly to state 326. In state 326, the process 300 determines the X-ray detector 202 should be focused or zoomed in or out. If yes, the process 300 adjusts a focusing element or a zoom element of the X-ray detector in state 328, and then proceeds to state 330. If no, the process 300 proceeds directly to state 330.

In state 330, X-rays are applied to the sample from the X-ray source 220. In state 332, the X-ray detector 202 detects X-rays that pass through the sample. The process 300 proceeds to state 334, where one or more signals are generated based on the received signals in state 330. Finally, in state 336 the process 300 displays an image based on the one or more received signals which can then be used to evaluate the sample.

Figure 11:
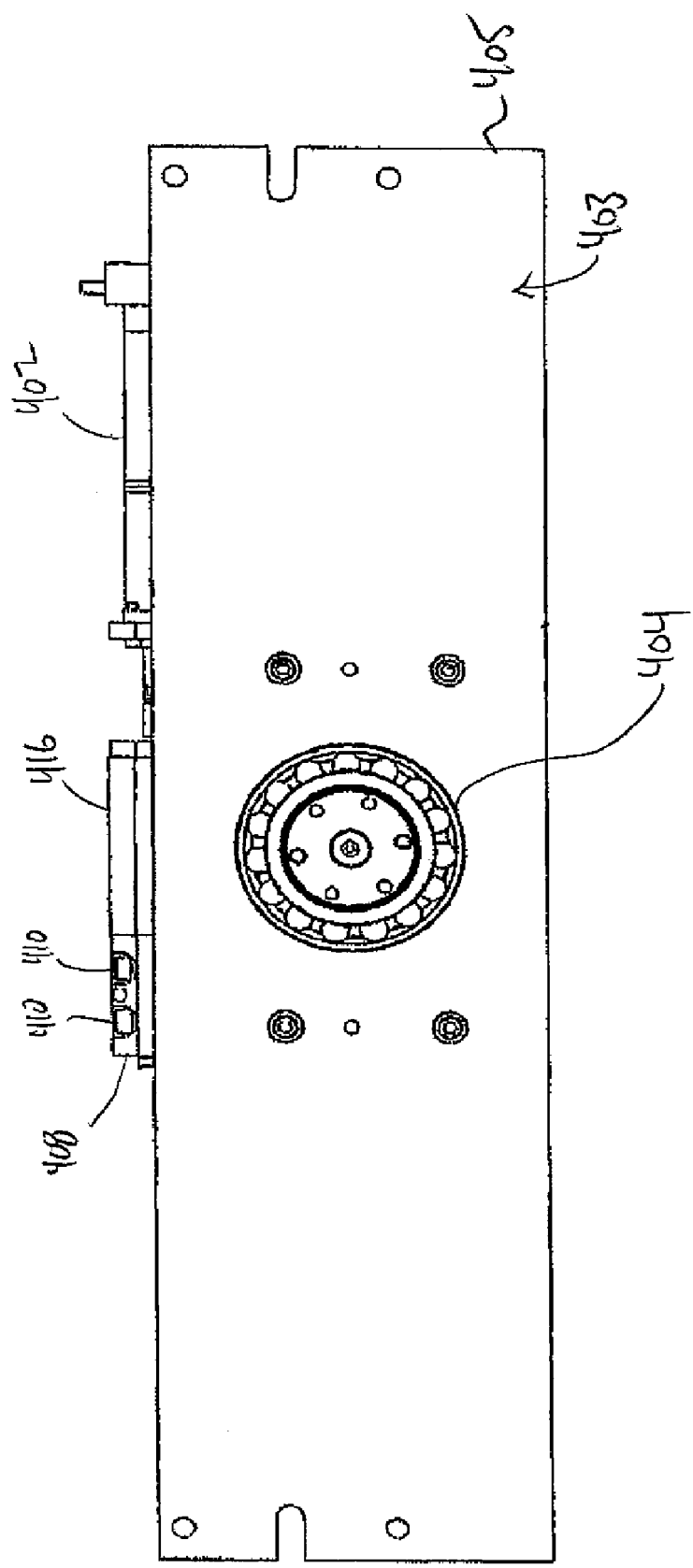
FIG. 11 is a front elevation view of a tilt mechanism.
Figure 12:
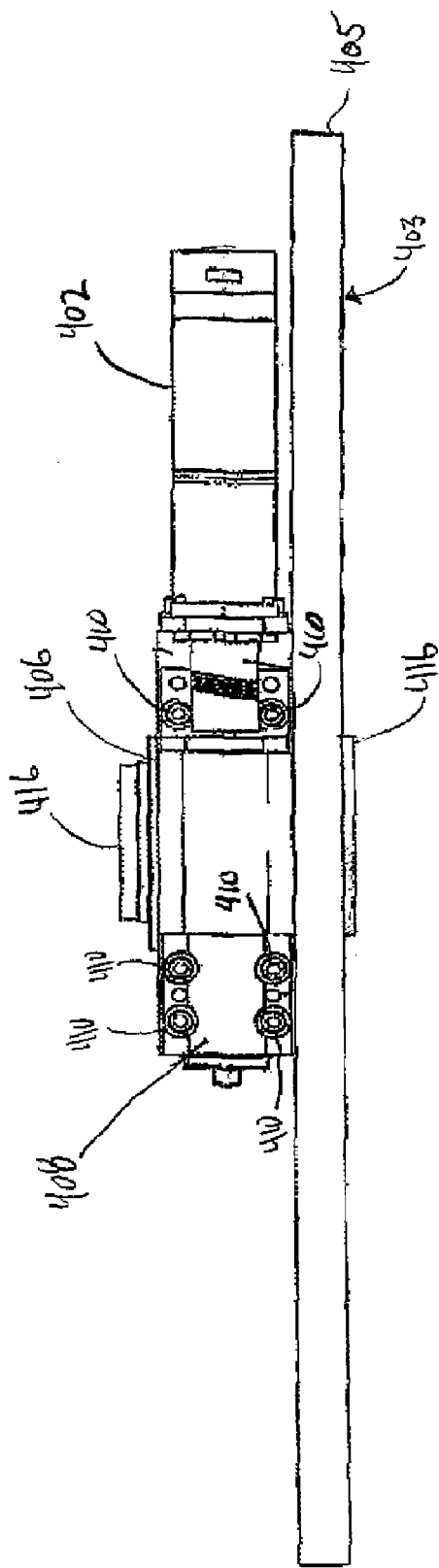
FIG. 12 is a top plan view of the tilt mechanism and a gear box assembly.
Figure 13:
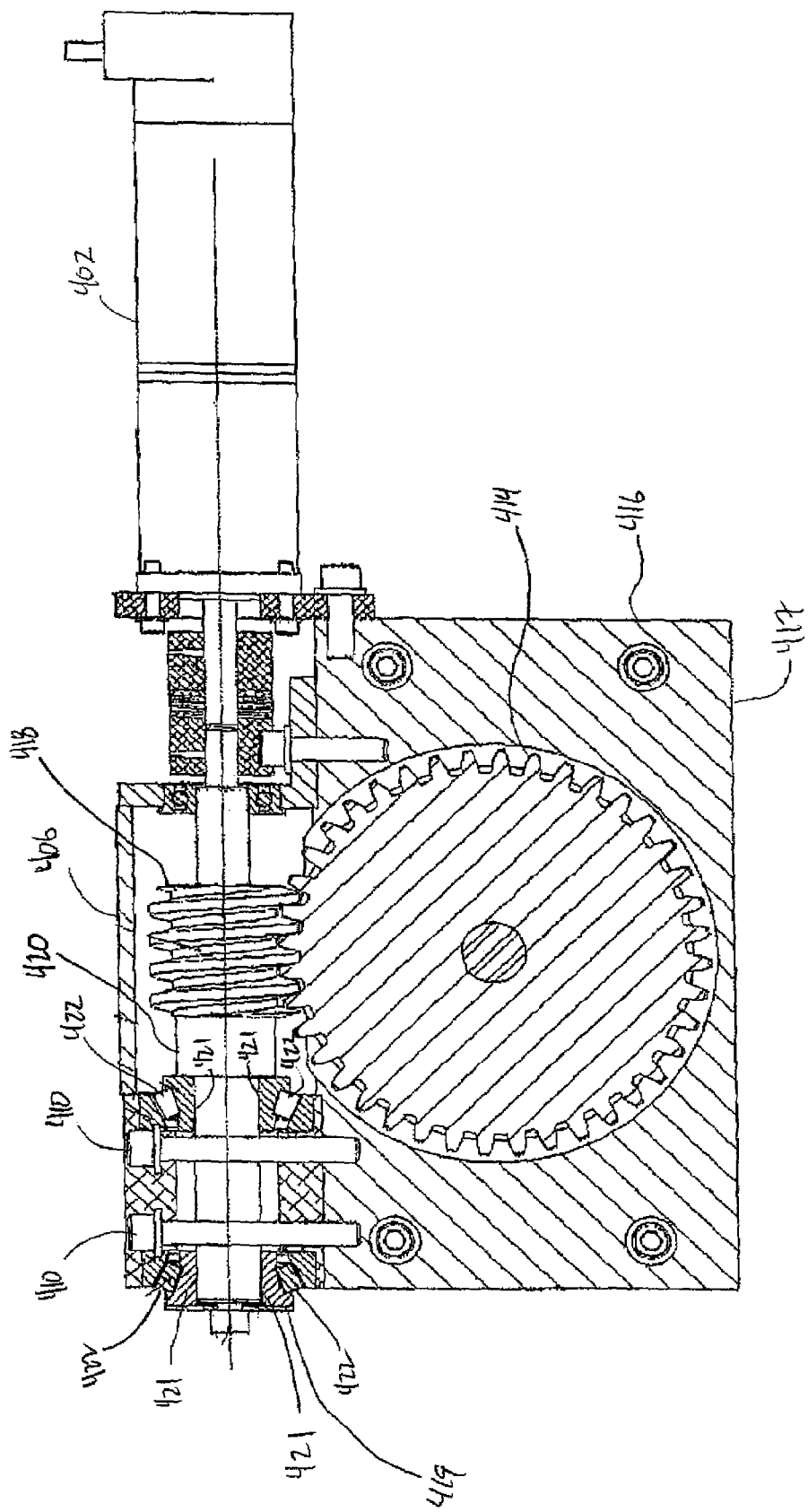
FIG. 13 is a front plan view of the gear box assembly illustrating a view of the components therein.

FIGS. 11-13 show aspects of one embodiment of a tilt mechanism 212 that can be used to rotate the X-ray source 220 and the X-ray detector 202 around the stage 106. Particular connecting structures between a tilt mechanism 212 and the X-ray source 220 and the X-ray detector 202 can vary based on the particular design of the inspection system housing, stage and other components due to, for example, sizing constraints. For example, in some embodiments the tilt mechanism 212 can connect directly to the tilt assembly 230, while in other embodiments there may be intervening structures between the tilt mechanism 212 and the tilt assembly 230, e.g., structure that is used for spacing, attaching, or rotating/tilting the tilt assembly in conjunction with the tilt mechanism 212. Specifically, FIG. 11 illustrates a front elevation view of a tilt mechanism 212 and a gear box assembly 416, FIG. 12 illustrates a top plan view of the tilt mechanism 212 gear box assembly 416, and FIG. 13 illustrates a front plan view of the gear box assembly 416. In this embodiment, surface 403 is disposed facing the tilt assembly 430.

A motor 402 coupled to the gear box assembly 416 is used to provide a driving force for rotating the tilt assembly 430. Bearing housing 408 is attached to a gear housing 417 by hold screws 410. The bearing housing 408 encloses bearing block 419 having bearings 422 and alignment surfaces 421, and is positioned around a drive shaft 420, which is coupled to the motor 402. A worm drive 418 (FIG. 13) on shaft 420 interacts with gear 414 disposed in the gear housing 417. When the motor 402 rotates the shaft 402, the worm drive 418 interacts with the gear 414 which in turn causes the tilt assembly to rotate. In this embodiment, the bearing 422 are positioned surrounding the shaft 420 such that the longitudinal axis of the bearings is at an angle with the longitudinal axis of the shaft 420. When sufficiently tightened, the hold down screws 410 through the "angled" bearings to apply pressure to the alignment surfaces and correspondingly to shaft 420 to eliminate any backlash or positional movement of the shaft 420, and eliminating undesired movement of the tilt assembly 430.

The tilt assembly 430 can be connected to a tilt mechanism in various ways. In some embodiments, a tilt mechanism has a stationary portion (e.g., connected to the inspection system housing 102) and the tilt assembly 430 is connected to a center portion rotational means (e.g., rotational means 404 FIG. 11) that is connected to the gear 414 so that is rotates when the gear 414 moves. In other embodiments, a rotational center portion of a tilt mechanism is connected to the inspection system housing 102 and the tilt mechanism and the tilt assembly 430 are connected such that they both rotate when the motor 402 is actuated and rotates the shaft 420, e.g., so that the gear 414 is stationary and the worm drive 418 "drives" around the gear 414 to move the X-ray source 220 and the X-ray detector 202.

It is also noted that the examples may be described as a process, which is depicted as a flowchart, a flow diagram, a structure diagram, or a block diagram. Although a flowchart may describe the operations as a sequential process, many of the operations can be performed in parallel or concurrently and the process can be repeated. In addition, the order of the operations may be re-arranged, operations not shown may be performed, or operations shown may be omitted depending on the circumstances. A process is terminated when its operations are completed. A process may correspond to a method, a function, a procedure, a subroutine, a subprogram, etc. When a process corresponds to a function, its termination corresponds to a return of the function to the calling function or the main function. The description of a process as a software program, electronic module, subroutine, subprogram, or a software module is a broad description of the operation and is not intended to require all embodiments to be implemented identically, unless expressly stated as such. Instead, one of skill in the art will recognize that such operations can typically be implemented in hardware, software, or firmware, and an operation that is described as a single program or module may also be implemented in two or more modules, submodules, programs or subprograms or subroutines.

Those of ordinary skill would understand that the various illustrative logical blocks, modules, and algorithm steps described in connection with the examples disclosed herein may be implemented as electronic hardware, computer software, or combinations of both which are part of or communicate with the inspection system. To clearly illustrate this interchangeability of hardware and software, various illustrative components, blocks, modules, circuits, and steps have been described above generally in terms of their functionality. The steps of a method or algorithm described in connection with the examples disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the disclosed methods.

Various embodiments of the invention have been described above, Although this invention has been described with reference to these specific embodiments, the descriptions are intended to be illustrative of the invention and are not intended to be limiting. Various modifications and applications may occur to those skilled in the art without departing from the true spirit and scope of the invention.

The invention claimed is:

1. An inspection apparatus, comprising:
  an X-ray source;
  an X-ray detector wherein the X-ray source and X-ray detector are positioned relative to each other such that a sample can be placed there between and such that X-rays emitted from the X-ray source passing through the sample can be detected by the X-ray detector;
  a positioning table comprising a stage configured to support a sample, the stage being positionable in an xy plane between the X-ray source and the X-ray detector for inspecting the sample;
  a housing enclosing the X-ray source, the X-ray detector, and the stage when the stage is positioned for inspecting a sample;
  a first access door connected to the housing, the first access door configured to be movable to an open position for loading and unloading the stage and to a closed position for inspecting the sample; and
  a first access aperture disposed in the housing, wherein the size of the first access door corresponds to the size of the first access aperture to prevent X-rays from exiting the housing through the first access aperture,
  wherein the stage is further positionable so as to extend through the first access aperture to a position exterior to the housing such that the entire stage can be moved to a position outside of the housing for loading and unloading a sample.

2. The apparatus of claim 1, wherein the stage comprises an attachment means for connecting the sample to the stage.

3. The apparatus of claim 1, wherein the first access aperture is at least about three inches wide and at least about twenty-five inches long.

4. The apparatus of claim 1, wherein the first access aperture is disposed between about twenty inches and about forty-five inches above a lowest portion of the housing for ease of loading and unloading the stage.

5. The apparatus of claim 1, the housing comprising a first portion configured as an operator station for controlling inspection of a sample, the operator station comprising a stage controller adapted to move the stage for inspecting the sample and to move the stage to a location interior to the housing and adjacent to the first access door in preparation for loading or unloading a sample, and from the location interior to the housing and adjacent to the first access door to a position between the X-ray source and the X-ray detector for inspection of the sample.

6. The apparatus of claim 5, further comprising one or more interlocks adapted to prevent the stage controller from moving the stage when the first access door is placed in the open position.

7. The apparatus of claim 6, wherein the positioning table is configured to be controlled by the stage controller to move the stage in the xy plane when the first access door is in the closed position, and wherein the positioning table is further configured to be controlled manually to move the stage when the first access door is in the open position.

8. The apparatus of claim 5, further comprising a window disposed in the housing for visually sighting a sample while it is being inspected 9. The apparatus of claim 1, further comprising
  a second access door connected to the housing; and
  a second access aperture disposed in the housing such that the stage is accessible for loading samples through the second access aperture, wherein the second access aperture is greater in length than the first access aperture to accommodate loading and unloading of a sample too large to fit through the first access door.

10. The apparatus of claim 1, further comprising
  a computer configured with inspection software and further configured to receive signals generated by the x-ray detector, wherein the inspection software is configured to generate images of the sample based on the signals received from the X-ray detector; and a display connected to the housing, the display in communication with the computer for displaying the images of the sample during inspection.

11. The apparatus of claim 1, further comprising
a source translation table connected to the X-ray source and configured to move the X-ray source along an imaging axis between the X-ray source and the X-ray detector for changing the distance between the X-ray source and the stage;
a detector translation table connected to the X-ray detector and configured to move the X-ray detector along the imaging axis to change the distance between the X-ray detector and the stage; and
a tilt plate connected to the source translation table and the detector translation table, the tilt plate configured to hold the X-ray source and the X-ray detector at a fixed position relative to each other along the imaging axis; and
a tilt assembly comprising a gearbox, the tilt assembly configured to rotate the X-ray source and the X-ray detector about the stage in a plane perpendicular to the xy plane so as to irradiate a sample on the stage at an oblique angle.

12. The apparatus of claim 11, wherein the X-ray detector further comprises a focusing element and a zoom element.

13. The apparatus of claim 1, further comprising a tilt mechanism connected to the X-ray source and the X-ray detector, the tilt mechanism comprising a gearbox assembly having a worm drive shaft and a bearing block surrounding a portion of the drive shaft for eliminating any backlash or positional movement of the drive shaft, the bearing block comprising bearings and alignment surfaces positioned around the drive shaft such that the longitudinal axis of the bearings is at an angle with the longitudinal axis of the drive shaft.

14. An inspection apparatus, comprising:
an X-ray source;
an X-ray detector wherein the X-ray source and X-ray detector are positioned relative to each other such that a sample can be placed there between and such that X-rays emitted from the X-ray source passing through the sample can be detected by the X-ray detector;
a positioning table comprising a stage configured to support a sample, the stage being positionable in an xy plane between the X-ray source and the X-ray detector for inspecting the sample;
a sample manipulator connected to the stage, the sample manipulator being configured to hold a sample at an angle relative to the xy plane, and further being configured to rotate the sample to one or more angles relative to the xy plane without moving the stage;
a housing enclosing the X-ray source, the X-ray detector, and the stage when the stage is positioned for inspecting a sample;
a first access door connected to the housing, the first access door configured to be movable to an open position for loading and unloading the stage and to a closed position for inspecting the sample; and
a first access aperture disposed in the housing, wherein the size of the first access door corresponds to the size of the first access aperture to prevent X-rays from exiting the housing through the first access aperture,
wherein the stage is further positionable from the interior of the housing so as to extend through the first access aperture to a position exterior to the housing such that at least a portion of the stage is positioned exterior to the housing for loading and unloading a sample.

15. A method of inspecting a sample with an X-ray inspection system having a X-ray source and an X-ray detector positioned relative to each other so that a sample can be placed there between and so that X-rays emitted from the X-ray source passing through the sample can be detected by the X-ray detector, the inspection system further having a housing, a first access aperture in the housing, and a first access door covering the first access aperture, the method comprising:
opening the first access door;
moving at least a portion of a stage through the first access aperture to a first position outside of the housing to receive a sample;
attaching a sample into a sample manipulator attached to the stage, the sample manipulator controllable to rotate the sample to a desired position for inspecting the sample without moving the stage;
moving the stage into the housing;
closing the first access door;
moving the stage to a second position for inspection of the sample;
rotating the sample using the sample manipulator;
applying X-rays to the sample;
receiving X-rays passing through the sample;
generating one or more signals based on the received X-rays; and
displaying an image of the sample for analysis based on the one or more signals.

16. The method of claim 15, wherein the first position is such that at least five inches of the stage extends outside of the housing when the stage is placed at the first position.

17. The method of claim 15, wherein the first position is such that at least ten inches of the stage extends outside of the housing when the stage is placed at the first position.

18. An inspection system, comprising:
an X-ray source;
an X-ray detector wherein the X-ray source and X-ray detector are positioned relative to each other such that a printed circuit board assembly can be placed there between and such that X-rays emitted from the X-ray source passing through the printed circuit board assembly can be detected by the X-ray detector;
a positioning table comprising a stage configured to support the printed circuit board assembly, the stage being positionable in an xy plane between the X-ray source and the X-ray detector for inspecting the printed circuit board assembly;
a housing enclosing the X-ray source, the X-ray detector and the stage when the stage is positioned for inspecting the printed circuit board assembly; and
the stage being positionable to a load/unload position outside of the housing such that the entire stage is outside of the housing at the load/unload position.

* * * * *

UNITED STATES PATENT AND TRADEMARK OFFICE
CERTIFICATE OF CORRECTION

| | | |
|---|---|---|
| PATENT NO. | : 7,529,338 B2 | Page 1 of 1 |
| APPLICATION NO. | : 11/677520 | |
| DATED | : May 5, 2009 | |
| INVENTOR(S) | : Fung et al. | |

It is certified that error appears in the above-identified patent and that said Letters Patent is hereby corrected as shown below:

Column 9, Line 29, please delete "210," and insert therefore, --210.--.

Column 15, Line 52, please delete "above," and insert therefore, --above.--.

Column 16, Line 53, in Claim 8, after "inspected", please insert --.--.

Signed and Sealed this

Eighth Day of December, 2009

David J. Kappos
*Director of the United States Patent and Trademark Office*